(12) United States Patent
Marseille et al.

(10) Patent No.: US 8,465,410 B2
(45) Date of Patent: Jun. 18, 2013

(54) HEART ASSIST SYSTEM

(75) Inventors: Oliver Marseille, Aachen (DE); Wolfgang Kerkhoffs, Aachen (DE); Oliver Schumacher, Aachen (DE)

(73) Assignee: Circulite, Inc., Teaneck, NJ (US)

( * ) Notice: Subject to any disclaimer, the term of this patent is extended or adjusted under 35 U.S.C. 154(b) by 0 days.

(21) Appl. No.: 13/419,745

(22) Filed: Mar. 14, 2012

(65) Prior Publication Data

US 2012/0172657 A1    Jul. 5, 2012

Related U.S. Application Data

(63) Continuation of application No. 11/627,444, filed on Jan. 26, 2007, now Pat. No. 8,157,720.

(60) Provisional application No. 60/743,183, filed on Jan. 27, 2006.

(51) Int. Cl.
*A61N 1/362* (2006.01)

(52) U.S. Cl.
USPC .................................. 600/16; 600/17; 600/18

(58) Field of Classification Search
USPC ....................................................... 600/16–18
See application file for complete search history.

(56) References Cited

U.S. PATENT DOCUMENTS

| 5,704,891 A * | 1/1998 | Mussivand ....................... 600/16 |
| 6,605,032 B2 * | 8/2003 | Benkowski et al. ............. 600/16 |
| 2005/0107658 A1 * | 5/2005 | Brockway ....................... 600/16 |

FOREIGN PATENT DOCUMENTS

| EP | 0928613 | 1/1998 |
| JP | 09-502375 | 3/1997 |
| JP | 10-85322 | 4/1998 |
| JP | 2005-000434 | 1/2006 |
| WO | 95-28185 | 10/1995 |
| WO | WO 03/075744 | 9/2003 |

OTHER PUBLICATIONS

European Search Report dated Jun. 13, 2012, issued in corresponding European Patent Application No. 07 71 7446.

Notice of Reasons for Rejection mailed Nov. 13, 2012, in corresponding Japanese Patent Application No. 2011-081546, and English language translation thereof (7 pages).

* cited by examiner

*Primary Examiner* — Rex R Holmes
(74) *Attorney, Agent, or Firm* — Wood, Herron & Evans, L.L.P.

(57) ABSTRACT

A supplemental blood flow system for assisting with blood circulation in a patient. The system includes a supplemental blood flow device implantable in the patient and a controller for directing electrical power to the supplemental blood flow device and controlling the flow rate of blood through the device. The controller includes first and second power inlets and a power outlet. The power outlet is adapted to be coupled to an electrical line leading to the supplemental blood flow device. A portable programming module may be coupled to at least one of the first and second power inlets and operable to allow pump operating parameters stored in the controller to be changed according to the needs of the patient.

17 Claims, 7 Drawing Sheets

HEART ASSIST SYSTEM

CROSS REFERENCE

This application is a continuation of U.S. application Ser. No. 11/627,444, filed Jan. 26, 2007 (issued as U.S. Pat. No. 8,157,720 on Apr. 17, 2012) which claims the benefit of U.S. Provisional Application Ser. No. 60/743,183, filed Jan. 27, 2006 (expired), the disclosures of which are fully incorporated by reference herein.

TECHNICAL FIELD

The present invention generally relates to systems for assisting with blood circulation in a patient and, in particular, ventricular assist devices and control systems.

BACKGROUND

A ventricular assist device (VAD) typically involves the use of a heart pump connected with various control and power source components. VAD systems are desirably portable so that a patient may move around during normal daily activities. Various devices are used to control and monitor the implantable blood pump associated with the system and the patient is permanently linked to the pump controller. Therefore, VAD systems should be as lightweight, small and convenient to wear as possible. A controller that is connected to the pump is adjusted by authorized personnel from time to time. This has generally been accomplished at specified locations such as in hospitals and doctors' offices. In addition, the controller should not be adjusted by unauthorized personnel. Some known manners of addressing these issues have involved the use of a control panel or programming module that is built into the controller worn by the patient and that is locked to prevent misuse or unauthorized use. Alternatively, the controller is linked to a complex and immobile base station control unit for programming purposes (e.g., pump speed adjustment). Unfortunately, incorporating the control panel or programming module into the portable unit worn by the patient increases the complexity, size and weight of the control unit. On the other hand, the use of an immobile base station forces the patient to go to a doctor's office or hospital for any required adjustment of pump speed.

SUMMARY

Generally, in a first aspect, a supplemental blood flow system for assisting with blood circulation in a patient is provided and comprises a supplemental blood flow device, a controller and a portable programming module. In this aspect, the controller directs electrical power to the supplemental blood flow device and controls the flow rate of blood through the device. The controller includes first and second power inlets and a power outlet with the power outlet adapted to be coupled to an electrical line leading to the supplemental blood flow device. The portable programming module is configured such that it can be coupled to at least one of the first and second power inlets of the controller and operable to allow pump operating parameters stored in the controller to be changed according to the needs of the patient. The supplemental blood flow device is configured such that it is implantable in the patient.

In other aspects, first and second power supply units may be connected to the first and second power inlets. At least one of the first and second power supply units may be electrically connected to the programming module. The power supply units may take various forms, such as batteries, AC to DC adaptors, DC to DC adaptors and combinations of these or other types of power supply units. The controller may be configured such that it may transmit data to a computer, such as through a wireless transmitter.

In another aspect, a supplemental blood flow system for assisting with blood circulation in a patient may comprise the supplemental blood flow device and controller as described above in combination with first and second power supply units capable of being electrically connected to the first and second power inlets of the controller. Other combinations of the various features described herein also fall within the scope of the present invention.

Various additional combinations, features and advantages of the invention will become more readily apparent to those of ordinary skill in the art upon review of the following detailed description of illustrative embodiments taken in conjunction with the accompanying drawings.

DETAILED DESCRIPTION OF THE ILLUSTRATIVE EMBODIMENTS

Figure 1:
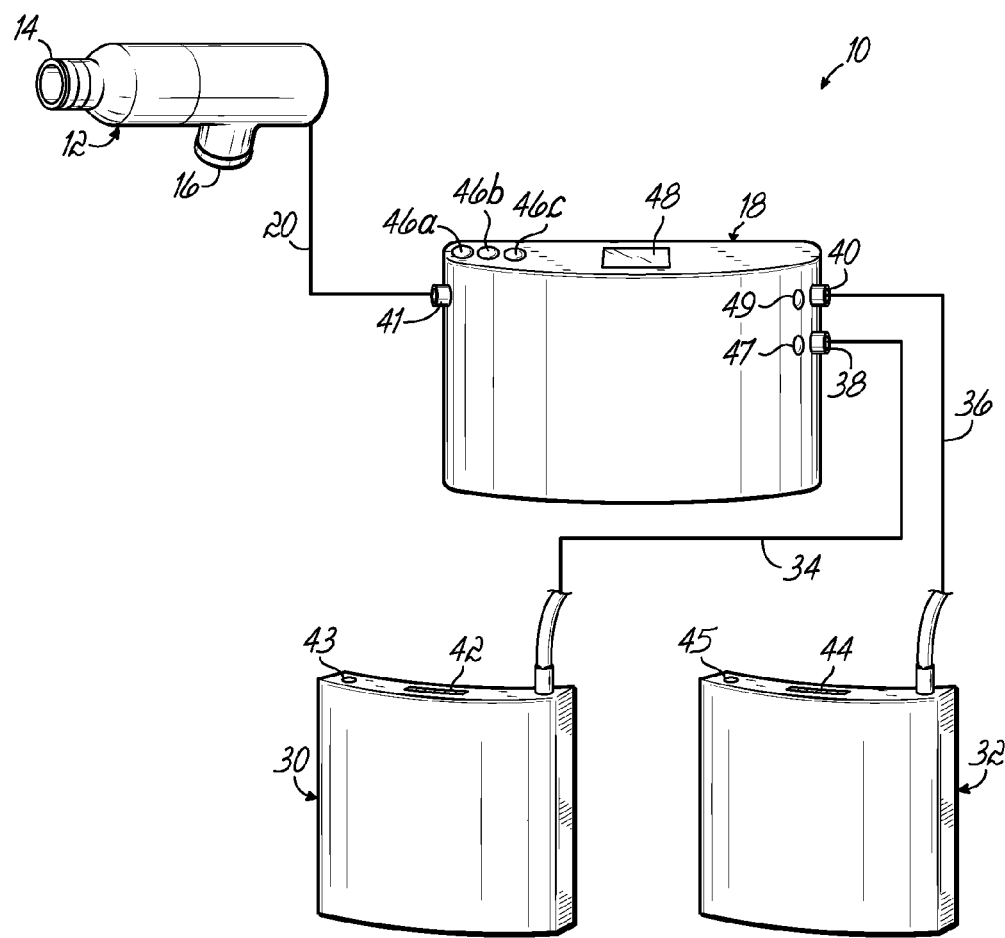
FIG. 1 is a schematic diagram of a system constructed in accordance with a first illustrative embodiment.

FIG. 1 illustrates a system 10 constructed in accordance with an illustrative embodiment of the invention. Specifically, system 10 includes a supplemental heart or blood pump 12 having an inlet 14 and an outlet 16. Supplemental heart pump 12 is adapted to be implanted within a patient and, for example, receives blood through the inlet 14 from the left side of the patient's heart (e.g., the left ventricle) and expels the blood into the patient's circulatory system through the outlet 16 and an attached conduit or catheter (not shown). Heart pump 12 is merely illustrative in nature and may be substituted with any appropriate heart pump or supplemental blood flow device. One example is disclosed in U.S. Pat. No. 6,116,862, the disclosure of which is hereby incorporated by reference herein. Heart pump 12 is connected to a controller 18 via an electrical line 20. Controller 18 supplies power to the heart pump 12 and controls the speed of the pump 12 in accordance with the medical needs of the patient. A primary battery 30 and a backup or secondary battery 32 are respectively coupled to the controller 18 by power lines 34, 36 connected to power inlet connectors 38, 40 on the controller 18. A power outlet connector 41 couples to electrical line 20. The controller 18 and batteries 30, 32 may be carried by a suitable belt or strap arrangement (not shown) to allow the patient to comfortably carry the components during his or her daily activities. All data may be stored in the controller by, for example, a flash memory device or other suitable memory component.

The batteries 30, 32, respectively, include charge indicator lights 42, 44. These indicator lights may, for example, comprise different colored LED's (light emitting diodes) such as red, yellow and green lights for indicating battery strength or charge to the user. Separate indicator lights 43, 45 may also be provided on the respective batteries 30, 32. For example, these indicator lights 43, 45 may comprise red LED's which, when lit, will indicate to the user that the associated battery 30 or 32 is not operating or is in need of recharging and/or replacement. The use of two separate batteries 30, 32 in this configuration allows the user a longer period of time away from a stationary power source, such as AC or other main power supplied in their home or other location. When the charge in the primary battery 30 falls below a predetermined level as, for example, sensed by the controller 18, the controller 18 will cause the secondary battery 32 to supply power to the controller 18 and to the pump 12. The controller 18 includes indicator lights 46a, 46b, 46c which may, for example, be red, yellow and green lights, respectively. The red light 46a can indicate that the pump 12 is stopped and/or indicate the need for some immediate repair or diagnostic action to address a problem with the system 10. This may be accompanied by an acoustic alarm. The yellow light 46b may indicate that inspection and/or routine maintenance is required, and the green light 46c may indicate normal operating mode. The display 48 indicates estimated remaining battery life in hours and minutes. Respective indicator lights 47, 49 associated with connectors 38, 40 may also be provided and, when lit, these red indicator lights 47, 49 can indicate the need to change the battery 30 or 32 coupled with the associated connector 38 or 40.

Figure 2:
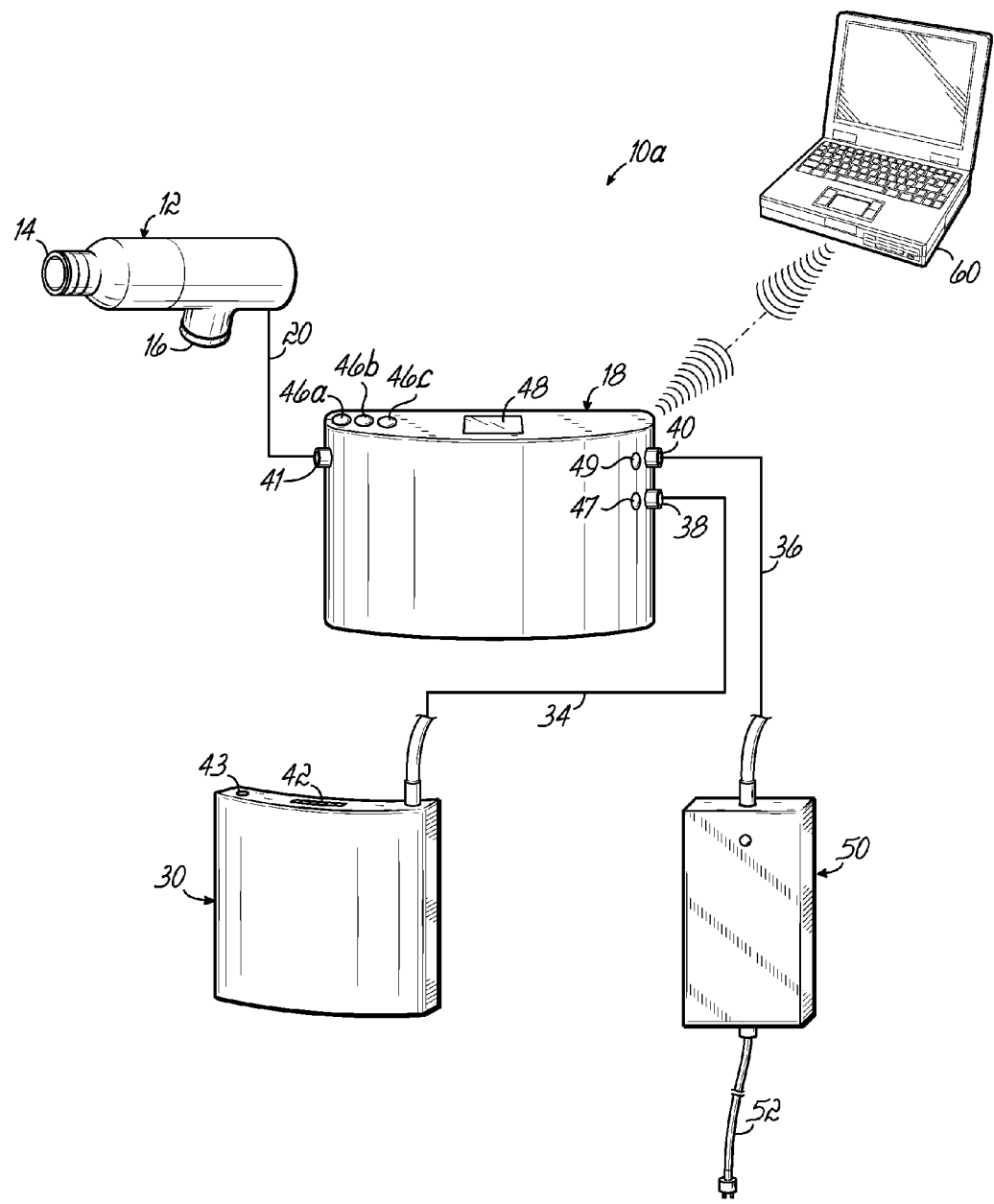
FIG. 2 is a schematic diagram of a system constructed in accordance with a second illustrative embodiment.

FIG. 2 illustrates an alternative system 10a. In each of the alternative systems to be described herein, like reference numerals indicate like elements in the various figures and therefore these elements do not require further duplicative description. FIG. 2 illustrates the fact that one of the batteries may be replaced by an adaptor unit 50 which may be plugged into an AC power supply via a plug 52 and thereby supply electrical power to the controller 18 and pump 12 in a manner similar to the battery 32 shown in FIG. 1, and via connector 40. As needed by the user, the adaptor 50 may be an AC to DC adaptor or a DC to DC adaptor. At the same time that adaptor 50 is supplying electrical power to controller 18 and pump 12, it may also be recharging battery 30. As another aspect shown in FIG. 2, a computer 60 may receive data from the controller for review by a physician. This data may be transferred in a wireless manner, or an optional hard cable (not shown) may be connected between controller 18 and computer 60. The data could be encoded so that the computer can detect and reject any false data. Such data may, for example, include pump speed, motor current, pump serial number, alarm status, or any data obtained by additional sensors or components associated with the system such as pressures, flow, temperature, heart rate, etc. and/or parameters obtained by any combination of the obtained data. The computer 60 may be limited, for example, to use for data acquisition and not used for changing any settings in the controller 18 associated with operating the pump, such as changing the pump speed. Such additional control and adjustment features may be reserved for other dedicated computers, controllers, etc., at a hospital and/or doctor's office and/or through the use of passcodes known only by authorized personnel.

Figure 3A:
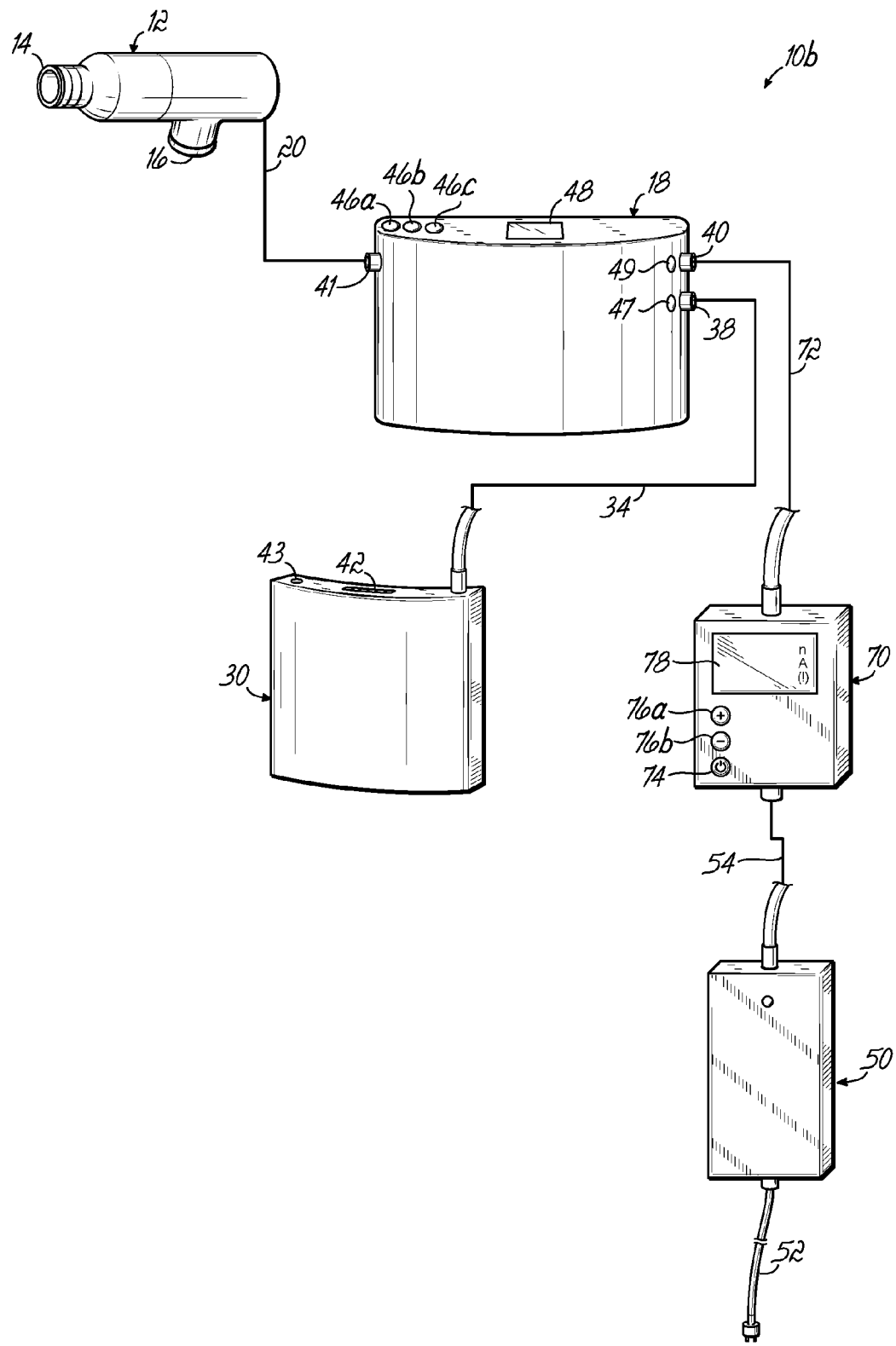
FIG. 3A is a schematic diagram of a system constructed in accordance with a third illustrative embodiment.

FIG. 3A illustrates another alternative system 10b in which a programming module 70 is connected between adaptor 50 and connector 40 and pump 12. Electrical power is therefore supplied through programming module 70 to controller 18 via connector 40. In addition, programming module 70 will allow control parameters, such as pump speed, to be changed in the controller 18. Programming module 70 may more specifically include an on/off control element such as a button 74, an adjustment element such as a button 76a for increasing the pump speed, an adjustment element such as a button 76b for decreasing the pump speed, and a display 78 for displaying parameters such as motor current, alarm status and pump speed. Adaptor 50 not only supplies electrical power for operating the programming module 70, but as mentioned above, may also supply power through to the controller 18 and/or to the pump 12, and/or for simultaneously recharging battery 30.

Figure 3B:
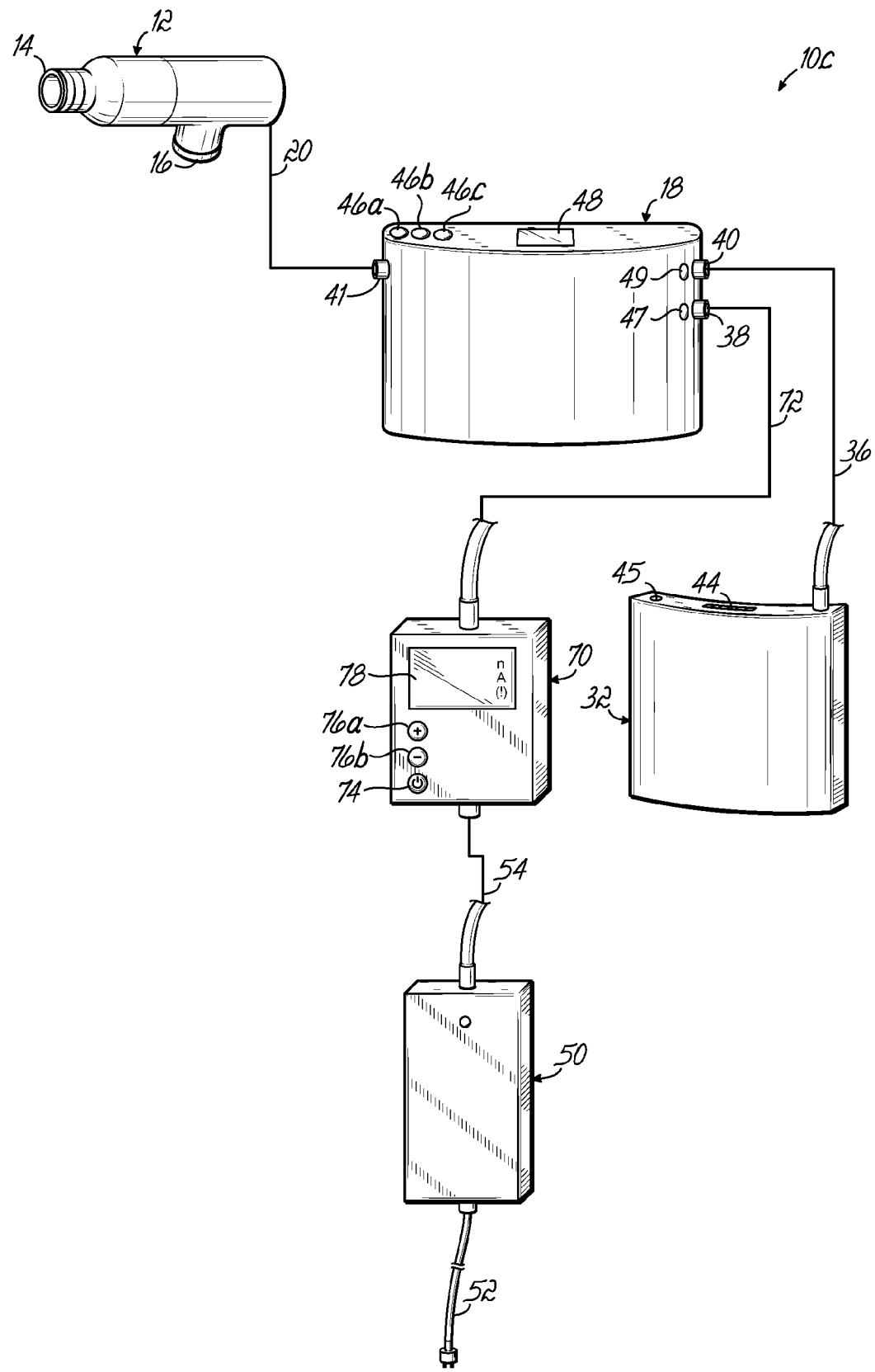
FIG. 3B is a schematic diagram of a system constructed in accordance with a fourth illustrative embodiment.

FIG. 3B illustrates another alternative system 10c which is similar to system 10b shown in FIG. 3A, except that the adaptor 50 and programming module 70 are respectively coupled to connector 38, as opposed to connector 40. In this example, battery 32 has been connected to connector 40 via power line 36. Thus, connectors 38, 40 may be interchangeably used when connecting any types of power supplies and the programming module 70. In this example, line 72 can carry relatively low current electronic data transmissions between module 70 and controller 18 and also carry higher current electronic power necessary for operating the pump 12.

Figure 3C:
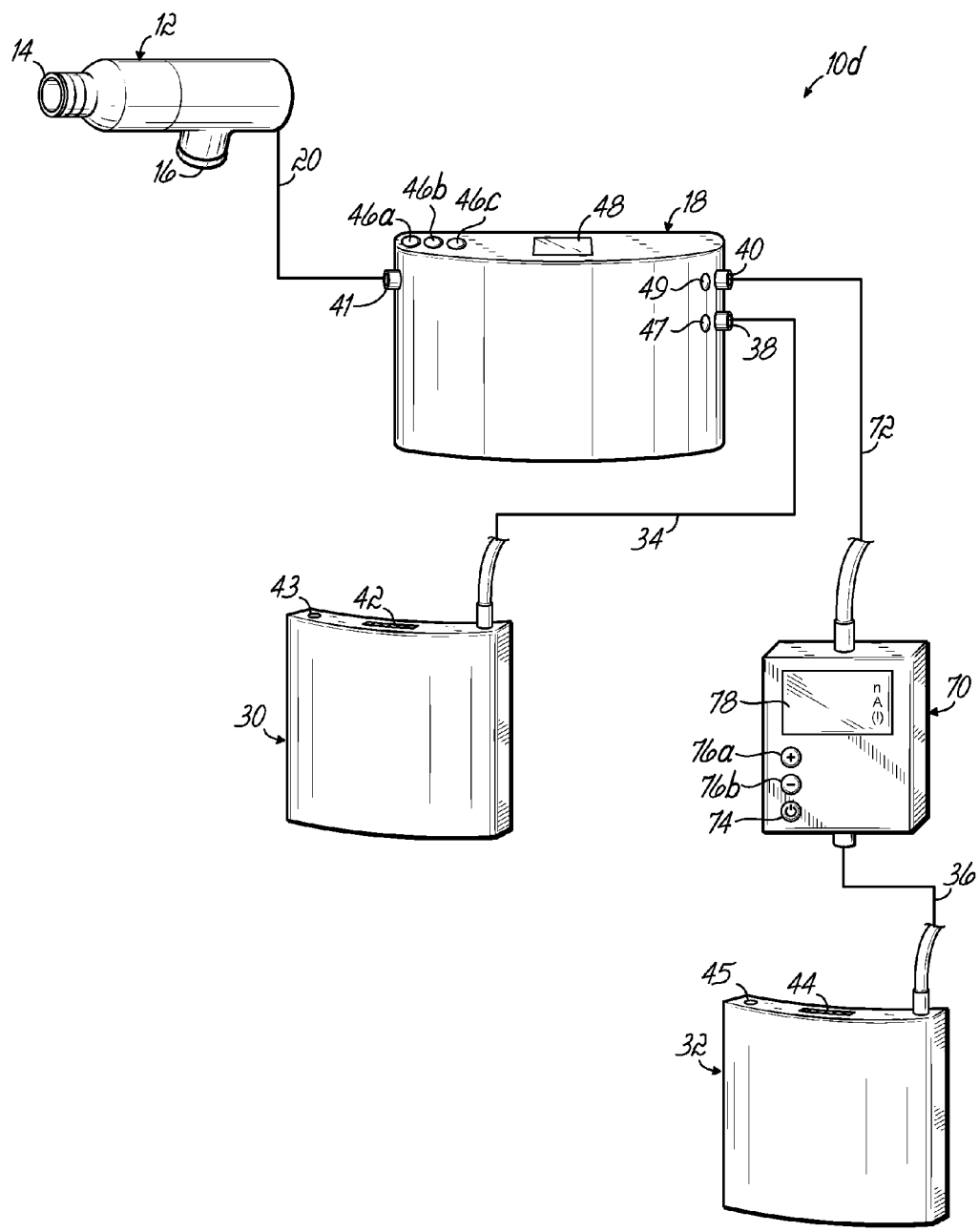
FIG. 3C is a schematic diagram of a system constructed in accordance with a fifth illustrative embodiment.

FIG. 3C illustrates another alternative system 10d which is similar to that shown in FIG. 3A, except that adaptor 50 has been replaced by battery 32 for powering programming module 70 and supplying power through to controller 18 and pump 12.

Figure 3D:
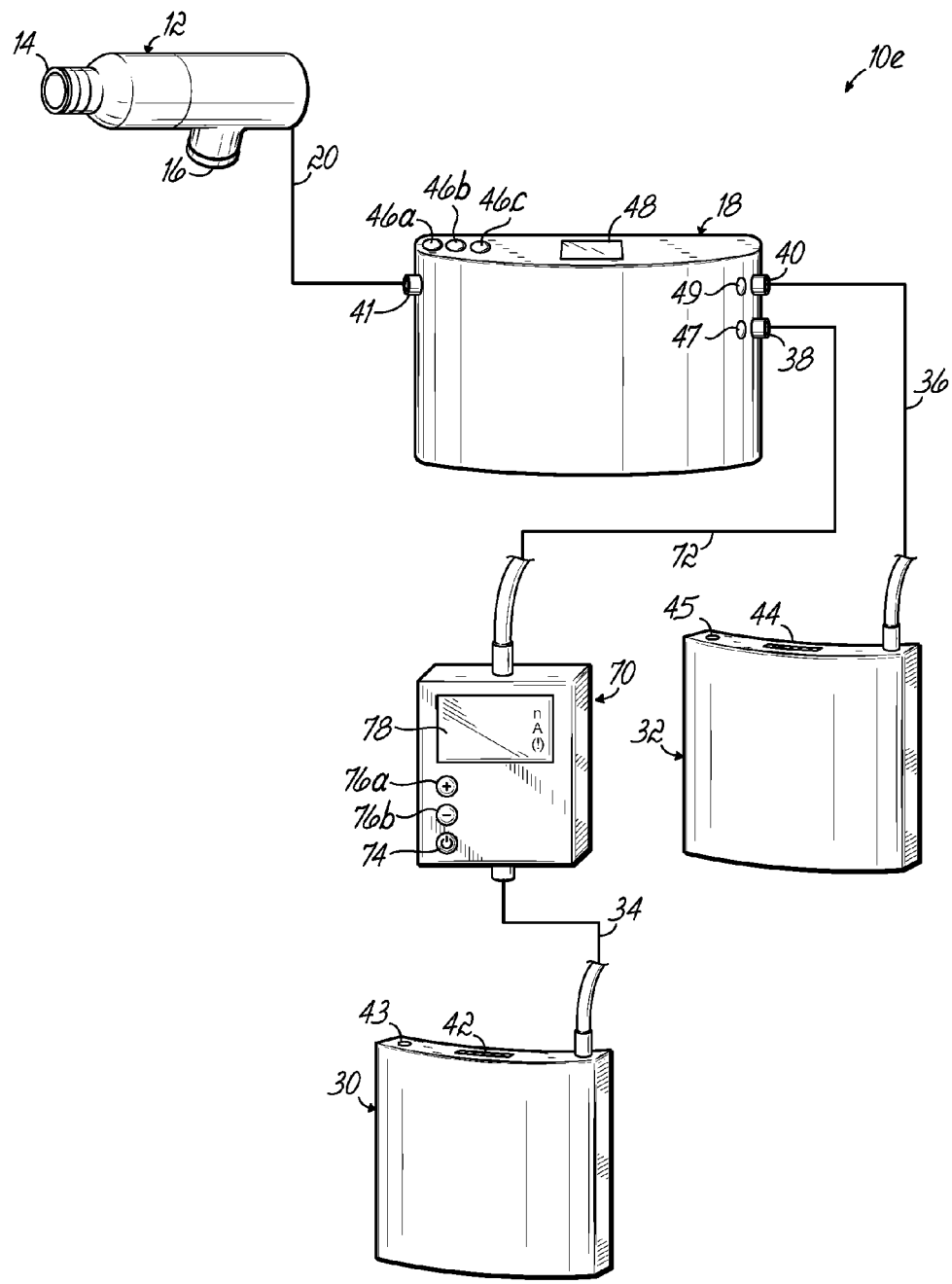
FIG. 3D is a schematic diagram of a system constructed in accordance with a sixth illustrative embodiment.

FIG. 3D illustrates another alternative system 10e which is similar to that shown in FIG. 3B except that adaptor 50 has been replaced by battery 30 for powering both the programming module 70 and also supplying power to the controller 18 and pump 12.

It will be appreciated that other configurations of the various components are also possible, as well as the addition of other suitable and useful components such as power supply components, control components or adaptors. One alternative, for example, is a 12 volt or 24 volt adaptor suitable for use in an automobile having a plug that may be inserted into a power receptacle in the automobile. The controller 18 may be designed to recognize when either an automotive adaptor or AC adaptor 50 is connected. Controller 18 can then use power from the connected adaptor as opposed to a connected battery so as to preserve battery life.

Figure 4:
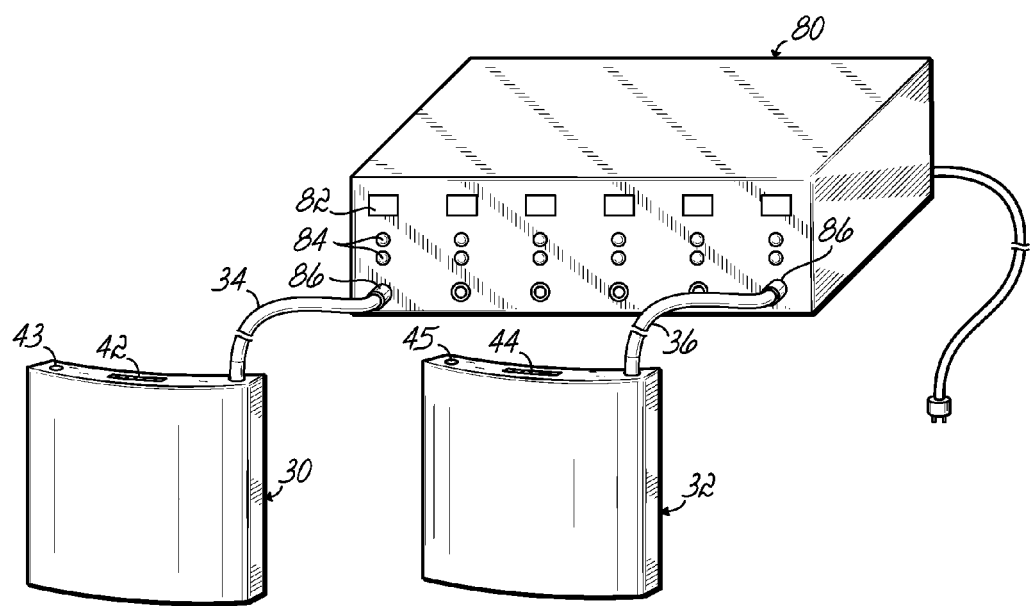
FIG. 4 is a perspective view of a battery recharge unit with two batteries connected thereto.

FIG. 4 illustrates a battery recharge unit 80 that may be plugged into a wall receptacle, for example, and may be used to recharge multiple batteries, such as batteries 30, 32 as shown. Recharge unit 80 may have a display 82 for indicating the remaining charging time, and may have various status indicator lights 84 for indicating charge status. For example, a red light may indicate that the battery is non-operative, a yellow light may indicate that the battery is charging, and a green light may indicate that the battery is fully charged. A number of connectors 86 may be provided for coupling several batteries to the charging unit 80.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A method of operating a supplemental blood flow system for assisting with blood circulation in a patient, the method comprising:
   directing electrical power to a supplemental blood flow device implanted in a patient through a controller electrically coupled to the supplemental blood flow device;
   adjusting parameters of a pump associated with the supplemental blood flow device using a portable programming module coupled temporarily to the controller;
   storing the parameters in the controller;
   coupling at least one power supply unit to the controller;
   coupling a battery to the controller;
   supplying power to the portable programming module through the controller with the at least one power supply unit; and
   supplying power to the battery through the controller with the at least one power supply unit to thereby charge the battery with power supplied through the controller.

2. The method of claim 1, wherein the at least one power supply unit comprises first and second power supply units and the method further comprises:
   respectively electrically coupling the first and second power supply units to the controller and using one of the power supply units to supply power to the portable programming module and the other of the power supply units to charge the battery.

3. The method of claim 1, further comprising:
   transmitting data from controller to a computer.

4. The method of claim 3, wherein transmitting the data further comprises wirelessly transmitting the data.

5. The method of claim 1, wherein the battery is a first battery, and the method further comprises:
   coupling a second battery to the controller in place of the at least one power supply unit; and
   using the controller to sense when the first battery is not supplying adequate electrical power and, as a result, directing electrical power from the second battery to the supplemental blood flow device.

6. The method of claim 5, wherein the second battery supplies power through the controller to the supplemental blood flow device.

7. The method of claim 1, further comprising:
   controlling a flow rate of blood through the supplemental blood flow device by applying the parameters stored in the controller to operate the pump.

8. The method of claim 1, wherein power supplied to the battery from the at least one power supply unit is delivered from the at least one power supply unit and through each of the controller and the portable programming module before arrival at the battery.

9. The method of claim 1, wherein the controller includes first and second power inlets and a power outlet electrically coupled to the supplemental blood flow device, the at least one power supply unit is coupled to the first power inlet of the controller, and the battery is coupled to the second power inlet of the controller.

10. A method of operating a supplemental blood flow system for assisting with blood circulation in a patient, the method comprising:
    directing electrical power to a supplemental blood flow device implanted in a patient through a controller electrically coupled to the supplemental blood flow device, the controller including a power outlet coupled to the supplemental blood flow device and also including first and second power inlets;
    adjusting parameters of a pump associated with the supplemental blood flow device using a portable programming module coupled temporarily to the controller at one of the first and second power inlets;
    storing the parameters in the controller;
    controlling a flow rate of blood through the supplemental blood flow device by applying the parameters stored in the controller to operate the pump;
    coupling at least one power supply unit to the controller at the first power inlet;
    coupling a battery to the controller at the second power inlet; and
    supplying power to the battery through the controller with the at least one power supply unit to thereby charge the battery with power supplied through the controller, wherein power supplied to the battery from the at least one power supply unit is delivered from the at least one power supply unit and through each of the controller and the portable programming module before arrival at the battery.

11. The method of claim 10, further comprising:
    supplying power to the portable programming module through the controller with the at least one power supply unit.

12. The method of claim 10, further comprising:
    transmitting data from controller to a computer.

13. The method of claim 12, wherein transmitting the data further comprises wirelessly transmitting the data.

14. The method of claim 10, wherein the battery is a first battery, and the method further comprises:
    coupling a second battery to the controller in place of the at least one power supply unit; and
    using the controller to sense when the first battery is not supplying adequate electrical power and, as a result, directing electrical power from the second battery through the controller to the supplemental blood flow device.

15. A method of operating a supplemental blood flow system for assisting with blood circulation in a patient, the method comprising:
    directing electrical power to a supplemental blood flow device implanted in a patient through a controller electrically coupled to the supplemental blood flow device, the controller including a power outlet coupled to the supplemental blood flow device and also including first and second power inlets;
    adjusting parameters of a pump associated with the supplemental blood flow device using a portable programming module coupled temporarily to the controller at one of the first and second power inlets;
    storing the parameters in the controller;
    controlling a flow rate of blood through the supplemental blood flow device by applying the parameters stored in the controller to operate the pump;
    coupling at least one power supply unit to the controller at the first power inlet;
    coupling at least one of a battery and the portable programming module to the controller at the second power inlet; and
    supplying power to the at least one of the battery and the portable programming module through the controller with the at least one power supply unit, wherein power supplied to the battery from the at least one power supply unit is delivered from the at least one power supply unit and through each of the controller and the portable programming module before arrival at the battery.

16. The method of claim 15, further comprising:
transmitting data from controller to a computer.

17. The method of claim 16, wherein transmitting the data further comprises wirelessly transmitting the data.

* * * * *